United States Patent
Morris et al.

(10) Patent No.: US 10,058,348 B2
(45) Date of Patent: Aug. 28, 2018

(54) APPARATUS AND METHOD FOR HEART VALVE REPAIR

(71) Applicant: St. Jude Medical, Cardiology Division, Inc., St. Paul, MN (US)

(72) Inventors: Benjamin E. Morris, Jeffersonville, IN (US); John Miser, Crestwood, KY (US); Gregory R. Furnish, Louisville, KY (US); Wayne A. Johnson, Jeffersonville, IN (US); Mark Griffin, Louisville, KY (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1060 days.

(21) Appl. No.: 14/375,986

(22) PCT Filed: Feb. 1, 2013

(86) PCT No.: PCT/US2013/024304
§ 371 (c)(1),
(2) Date: Jul. 31, 2014

(87) PCT Pub. No.: WO2013/116617
PCT Pub. Date: Aug. 8, 2013

(65) Prior Publication Data
US 2014/0379002 A1 Dec. 25, 2014

Related U.S. Application Data

(60) Provisional application No. 61/594,122, filed on Feb. 2, 2012.

(51) Int. Cl.
*A61B 17/122* (2006.01)
*A61B 17/08* (2006.01)
(Continued)

(52) U.S. Cl.
CPC .. *A61B 17/32056* (2013.01); *A61B 17/00234* (2013.01); *A61B 17/0644* (2013.01);
(Continued)

(58) Field of Classification Search
CPC ........ A61F 2/24; A61F 2/2445; A61F 2/2448; A61F 2/2451; A61F 2/2454;
(Continued)

(56) References Cited

U.S. PATENT DOCUMENTS

| 5,041,129 A | 8/1991 | Hayhurst et al. |
| 5,098,440 A * | 3/1992 | Hillstead ............... A61B 17/221 606/108 |

(Continued)

FOREIGN PATENT DOCUMENTS

| AU | 2002300522 B2 | 1/2007 |
| WO | 9620749 A1 | 7/1996 |

(Continued)

OTHER PUBLICATIONS

International Preliminary Report on Patentability for Application No. PCT/US2012/023437 dated Aug. 6, 2013.

(Continued)

*Primary Examiner* — Julian W Woo
(74) *Attorney, Agent, or Firm* — Lerner, David, Littenberg, Krumholz & Mentlik, LLP

(57) ABSTRACT

A method of gathering tissue of a heart valve leaflet 2 may include inserting an elongated catheter assembly 12 to a position adjacent the heart valve leaflet, the catheter assembly including a capture tool 22 and a tissue support member 30. The capture tool 22 and the tissue support member 30 may each be independently moveable between a retracted position and an extended position. Partially retracting the capture tool 22 with the tissue support member 30 in the extended position gathers tissue 15 of the heart valve leaflet 2 between the capture tool and the tissue support member. A clip 55 may then be applied from the catheter assembly 12 to the gathered tissue 15 to hold the tissue substantially in a gathered configuration.

16 Claims, 9 Drawing Sheets

(51) Int. Cl.
  A61B 17/128 (2006.01)
  A61B 17/3205 (2006.01)
  A61B 17/00 (2006.01)
  A61F 2/24 (2006.01)
  A61B 17/064 (2006.01)
  A61B 17/12 (2006.01)
  A61B 17/221 (2006.01)

(52) U.S. Cl.
  CPC .......... *A61B 17/083* (2013.01); *A61B 17/122* (2013.01); *A61B 17/128* (2013.01); *A61B 17/12013* (2013.01); *A61F 2/2457* (2013.01); A61B 2017/00243 (2013.01); A61B 2017/00292 (2013.01); A61B 2017/00349 (2013.01); A61B 2017/00783 (2013.01); A61B 2017/00867 (2013.01); A61B 2017/0645 (2013.01); A61B 2017/2212 (2013.01); A61B 2017/2215 (2013.01)

(58) Field of Classification Search
  CPC ............. A61F 2/2457; A61B 17/32056; A61B 17/128; A61B 17/122; A61B 17/0644; A61B 17/12013; A61B 17/083; A61B 2017/00349; A61B 2017/00783; A61B 2017/00867; A61B 17/00234; A61B 2017/2215; A61B 2017/2212; A61B 2017/00292; A61B 17/1227; A61B 17/1285; A61B 17/22031; A61B 17/1221; A61B 2017/00358; A61B 2017/2217; A61B 2017/22042; A61B 2017/22044; A61B 17/00358; A61B 17/00783; A61B 17/2215; A61B 17/2217; A61B 17/22042; A61B 17/22044; A61B 17/221; A61B 2017/00243; A61B 2017/0645
  See application file for complete search history.

(56) References Cited

U.S. PATENT DOCUMENTS

| | | | |
|---|---|---|---|
| 5,156,608 A | 10/1992 | Troidl et al. | |
| 5,499,991 A | 3/1996 | Garman et al. | |
| 5,601,573 A | 2/1997 | Fogelberg et al. | |
| 5,741,278 A | 4/1998 | Stevens | |
| 5,749,879 A | 5/1998 | Middleman et al. | |
| 5,921,993 A | 7/1999 | Yoon | |
| 6,258,105 B1 | 7/2001 | Hart et al. | |
| 6,352,503 B1* | 3/2002 | Matsui | A61B 1/00071 600/104 |
| 6,440,152 B1 | 8/2002 | Gainor et al. | |
| 6,461,366 B1* | 10/2002 | Seguin | A61B 17/00234 606/139 |
| 6,520,975 B2* | 2/2003 | Branco | A61B 17/00008 600/104 |
| 6,569,182 B1 | 5/2003 | Balceta et al. | |
| 6,626,930 B1 | 9/2003 | Allen et al. | |
| 6,752,813 B2 | 6/2004 | Goldfarb et al. | |
| 6,945,978 B1 | 9/2005 | Hyde | |
| 7,011,669 B2 | 3/2006 | Kimblad | |
| 7,464,712 B2 | 12/2008 | Oz et al. | |
| 7,569,062 B1 | 8/2009 | Kuehn et al. | |
| 7,758,595 B2 | 7/2010 | Allen et al. | |
| 8,652,146 B2* | 2/2014 | Hewitt | A61B 17/00234 606/113 |
| 8,777,966 B2 | 7/2014 | Dale et al. | |
| 8,951,285 B2 | 2/2015 | Sugimoto et al. | |
| 9,456,812 B2* | 10/2016 | Finch | A61B 17/0057 |
| 2001/0016750 A1 | 8/2001 | Malecki et al. | |
| 2002/0010388 A1 | 1/2002 | Taylor et al. | |
| 2002/0013571 A1 | 1/2002 | Goldfarb et al. | |
| 2002/0035390 A1 | 3/2002 | Schaldach et al. | |
| 2002/0049457 A1 | 4/2002 | Kaplan et al. | |
| 2002/0107531 A1 | 8/2002 | Schreck et al. | |
| 2002/0183768 A1 | 12/2002 | Deem et al. | |
| 2003/0065335 A1 | 4/2003 | Guido et al. | |
| 2003/0093071 A1 | 5/2003 | Hauck et al. | |
| 2003/0120264 A1 | 6/2003 | Lattouf | |
| 2004/0030335 A1 | 2/2004 | Zenati et al. | |
| 2004/0039442 A1 | 2/2004 | St. Goar et al. | |
| 2004/0087985 A1 | 5/2004 | Loshakove et al. | |
| 2004/0176784 A1 | 9/2004 | Okada | |
| 2004/0181238 A1 | 9/2004 | Zarbatany et al. | |
| 2004/0193185 A1 | 9/2004 | McBrayer | |
| 2005/0004583 A1 | 1/2005 | Oz et al. | |
| 2005/0090837 A1 | 4/2005 | Sixto et al. | |
| 2005/0096671 A1 | 5/2005 | Wellman et al. | |
| 2005/0107871 A1 | 5/2005 | Realyvasquez et al. | |
| 2005/0125011 A1 | 6/2005 | Spence et al. | |
| 2005/0143763 A1 | 6/2005 | Ortiz et al. | |
| 2005/0149072 A1 | 7/2005 | DeVries et al. | |
| 2005/0177176 A1 | 8/2005 | Gerbi et al. | |
| 2005/0250986 A1* | 11/2005 | Rothe | A61B 1/0014 600/102 |
| 2005/0251161 A1 | 11/2005 | Saadat et al. | |
| 2006/0009800 A1 | 1/2006 | Christianson et al. | |
| 2006/0089671 A1 | 4/2006 | Goldfarb et al. | |
| 2006/0122633 A1 | 6/2006 | To et al. | |
| 2006/0173422 A1 | 8/2006 | Reydel et al. | |
| 2006/0173473 A1 | 8/2006 | Bob | |
| 2007/0049952 A1 | 3/2007 | Weiss | |
| 2007/0093857 A1 | 4/2007 | Rogers et al. | |
| 2007/0102474 A1 | 5/2007 | Shelton et al. | |
| 2007/0102475 A1 | 5/2007 | Ortiz et al. | |
| 2007/0142846 A1 | 6/2007 | Catanese et al. | |
| 2007/0162056 A1 | 7/2007 | Gerbi et al. | |
| 2007/0197858 A1 | 8/2007 | Goldfarb et al. | |
| 2007/0198032 A1 | 8/2007 | Ortiz | |
| 2007/0225734 A1 | 9/2007 | Bell et al. | |
| 2008/0125796 A1 | 5/2008 | Graham | |
| 2008/0234705 A1 | 9/2008 | Cropper et al. | |
| 2008/0255427 A1 | 10/2008 | Satake et al. | |
| 2008/0294175 A1 | 11/2008 | Bardsley et al. | |
| 2008/0300624 A1 | 12/2008 | Schwemberger et al. | |
| 2008/0319455 A1 | 12/2008 | Harris et al. | |
| 2009/0062852 A1 | 3/2009 | Marino | |
| 2009/0118744 A1 | 5/2009 | Wells et al. | |
| 2009/0125038 A1 | 5/2009 | Ewers et al. | |
| 2009/0149870 A1 | 6/2009 | Jugenheimer et al. | |
| 2011/0054521 A1 | 3/2011 | Ventura et al. | |
| 2011/0077668 A1 | 3/2011 | Gordon et al. | |
| 2011/0087242 A1 | 4/2011 | Pribanic et al. | |
| 2011/0093009 A1* | 4/2011 | Fox | A61B 17/0057 606/216 |
| 2011/0114700 A1 | 5/2011 | Baxter, III et al. | |
| 2011/0230897 A1 | 9/2011 | Palermo et al. | |
| 2011/0313432 A1 | 12/2011 | Miles et al. | |
| 2012/0022532 A1 | 1/2012 | Garrison | |
| 2012/0109159 A1 | 5/2012 | Jordan et al. | |
| 2012/0226291 A1 | 9/2012 | Malizia et al. | |
| 2012/0277853 A1* | 11/2012 | Rothstein | A61B 17/064 623/2.11 |
| 2013/0046332 A1 | 2/2013 | Jones et al. | |
| 2014/0039607 A1 | 2/2014 | Kovach | |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 2002000121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |

(56) References Cited

FOREIGN PATENT DOCUMENTS

| WO | 2013019415 A1 | 2/2013 |
|---|---|---|
| WO | 2013116617 A1 | 8/2013 |
| WO | 2014022464 A1 | 2/2014 |

OTHER PUBLICATIONS

International Search Report and Written Opinion for Application No. PCT/US2013/023082 dated Oct. 1, 2013.
International Search Report and Written Opinion for Application No. PCT/US2013/024304 dated Jul. 5, 2013.
International Search Report and Written Opinion for Application No. PCT/US2013/052822 dated Jan. 21, 2014.
International Search Report and Written Opinion for Application No. PCT/US2013/052838 dated Oct. 11, 2013.
International Search Report and Written Opinion for Application No. PCT/US2013/052843 dated Oct. 11, 2013.
International Search Report and Written Opinion for Application No. PCT/US2013/065360 dated Apr. 23, 2014.
International Search Report for Application No. PCT/US2012/023437 dated Apr. 24, 2012.
International Search Report for Application No. PCT/US2013/023077 dated May 14, 2013.
International Search Report for Application No. PCT/US2013/052832 dated Jan. 15, 2014.

\* cited by examiner

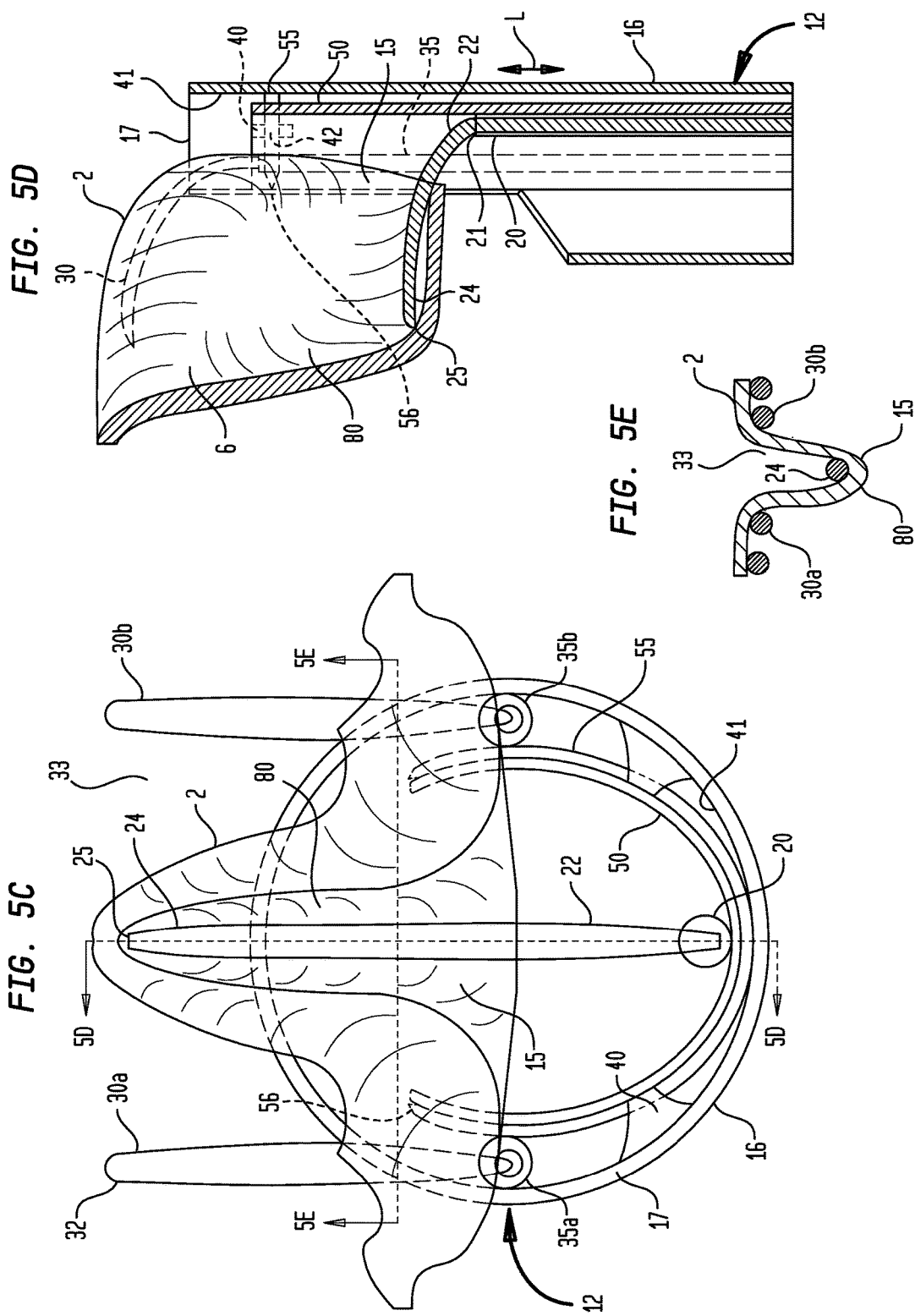

APPARATUS AND METHOD FOR HEART VALVE REPAIR

CROSS-REFERENCE TO RELATED APPLICATION

This application is a national phase entry under 35 U.S.C. § 371 of International Applicational No. PCT/US2013/024304 filed Feb. 1, 2013, published in English, which claims the benefit of the filing date of U.S. Provisional Patent Application No. 61/594,122 filed Feb. 2, 2012, the disclosures of which are hereby incorporated by reference herein.

BACKGROUND OF THE INVENTION

The present invention is related to heart valve repair, and more particularly to devices, systems, and methods for minimally invasive repair of a heart valve leaflet.

Properly functioning heart valves can maintain unidirectional blood flow in the circulatory system by opening and closing, depending on the difference in pressure from one side of the valve to the other. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be ruptured. As a result, the valve is not properly held in a closed condition. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to return to the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

Methods and devices for gathering of heart valve leaflet tissue are disclosed. A method of gathering tissue of a heart valve leaflet may include inserting an elongated catheter assembly to a position adjacent the heart valve leaflet, the catheter assembly including a capture tool and a tissue support member having at least two spaced apart support elements, the capture tool and the tissue support member each being independently moveable between a retracted position and an extended position. Then, the capture tool may be moved from the retracted position to the extended position, and the tissue support member may be moved from the retracted position to the extended position, the moving step being conducted so that the capture tool is positioned on one side of the heart valve leaflet and the tissue support member is positioned on another side of the heart valve leaflet opposite the one side. Next, the capture tool may be partially retracted from the extended position toward the retracted position to force tissue of the heart valve leaflet between the support elements of the tissue support member, the tissue being formed into a gathered configuration. A clip from the catheter assembly may be applied to the tissue so as to hold the tissue substantially in the gathered configuration.

Each support element may include a loop having a distal end, the distal ends of the loops being spaced from one another by a gap. The moving step may include sliding the distal ends of the loops between adjacent chordae tendineae of the heart valve leaflet and underneath the heart valve leaflet. The gathered configuration may be in the shape of a V. The catheter assembly may extend in a longitudinal direction, and the moving step may include moving a distal end of the tissue support member distally in the longitudinal direction and laterally away from the capture tool in a direction transverse to the longitudinal direction.

A distal end of the capture tool may have a hook shape in the extended position. The capture tool may include a grasping wire slidably disposed in a containment tube, and the moving step may include sliding a distal portion of the grasping wire out from the containment tube so that the distal portion of the grasping wire changes from a linear shape to a hook shape.

The catheter assembly may also include a retaining arm moveable between a first position for retaining the clip and a second position for releasing the clip, and the step of applying the clip may include moving the retaining arm from the first position to the second position to release the clip for application to the tissue. The clip may be biased from an open condition to a clamping condition, the retaining arm may hold the clip in the open condition, and the step of moving the retaining arm from the first position to the second position may release the clip for movement to the clamping condition.

A device for gathering tissue of a heart valve leaflet may include an elongated tube, a tissue support member moveable relative to the tube between a retracted position and an extended position, the tissue support member having at least two spaced apart support elements, and a capture tool moveable relative to the tube and between the support elements between a retracted position and an extended position. The capture tool and the tissue support member may be operable to capture tissue of the heart valve leaflet therebetween, such that the captured tissue has a gathered configuration.

The support elements may be made from a memory metal. The gathered configuration may be in the shape of a V. The elongated tube may extend in a longitudinal direction, and distal ends of the support elements may be adapted to move laterally away from the capture tool in a direction transverse to the longitudinal direction when the support elements move from the retracted position to the extended position. The device may also include an operating handle having an actuating member adapted to control movement of the tissue support member between the retracted and extended positions. Each support element may include a loop having a distal end, the distal ends of the loops being spaced from one another by a gap.

A distal end of the capture tool may have a hook shape in the extended position. The capture tool may include a grasping wire slidably disposed in a containment tube, and a distal portion of the grasping wire may be adapted to change from a linear shape to a hook shape when the distal portion of the grasping wire is extended out from the containment tube. The grasping wire may be made from a memory metal. The device may also include an operating handle having an actuating member adapted to control movement of the grasping wire between retracted and extended positions and movement of the containment tube between retracted and extended positions.

Operation of the actuating member may control simultaneous movement of the grasping wire and the containment tube. The actuating member may have first and second portions that are moveable relative to one another, the first portion being adapted to control movement of the grasping wire and the second portion being adapted to control movement of the containment tube. The first portion may be adapted to control movement of the grasping wire independently of movement of the containment tube.

The device may also include a releasable clip adapted to be applied to the tissue for holding the tissue in the gathered configuration. The device may also include a retaining arm moveable between a first position for retaining the clip and a second position for releasing the clip for application to the tissue. The clip may be biased from an open condition to a clamping condition, the retaining arm in the first position holding the clip in the open configuration, and the retaining arm in the second position releasing the clip for application to the tissue. The device may also include an operating handle having an actuating member adapted to control movement of the retaining arm between the first position and the second position.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 5C is a top plan view of the distal portion of the device of FIG. 2A, showing a portion of the posterior leaflet captured between the hook and the support loops;

FIG. 5D is a longitudinal cross-sectional view of the distal portion of the device of FIG. 2A, taken along line 5D-5D of FIG. 5C;

FIG. 5E is a diagrammatic partial cross-sectional view of the posterior mitral valve leaflet of FIG. 5C, taken along line 5E-5E of FIG. 5C, and showing the leaflet tissue gathered in a V-shaped pleat;

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
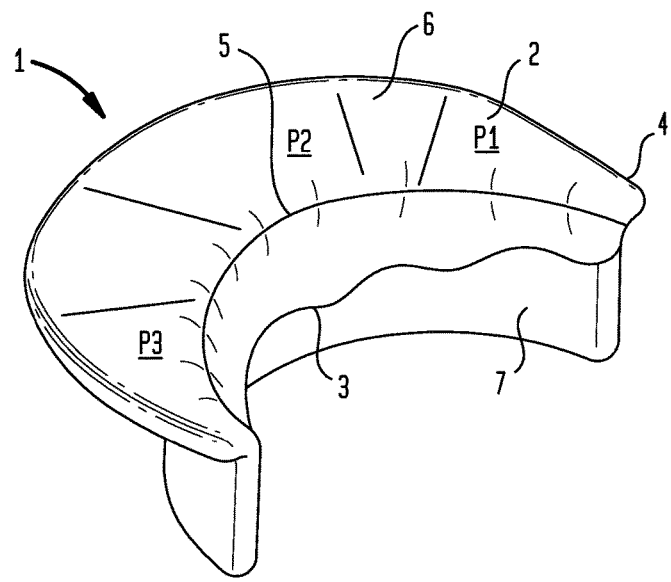
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3. Chordae tendineae 8 (FIG. 2A) may connect the lower portion 7 of the posterior leaflet 2 to the papillary muscles of the left ventricle 9.

Figure 2A:
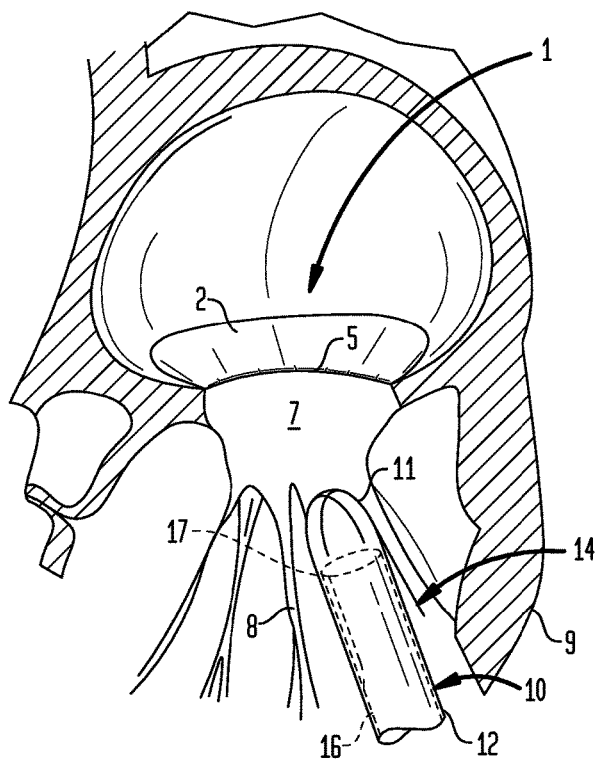
FIGS. 2A, 3A, 4A, and 5A are partial cross-sectional views of the human heart, showing the mitral valve and the steps of operating one embodiment of a device for gathering of heart valve leaflet tissue.
Figure 2B:
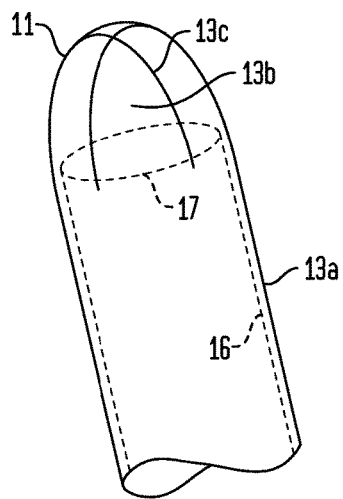
FIG. 2B is an enlarged front perspective view of the distal portion of the device shown in FIG. 2A.

Referring to FIG. 2A, an exemplary device 10 for gathering of heart valve leaflet tissue includes an elongated catheter assembly 12 adapted to be inserted through the apex of a human heart so that a distal portion 14 of the catheter assembly may reach the patient's mitral valve 1 for repair thereof.

The catheter assembly 12 includes an outer tube 16, the distal end 17 of which has an open side 19 and a closed side 41. An atraumatic tip 11 attached to a sleeve 13a extending proximally from the tip is longitudinally slidable between a deployed condition protruding distally beyond the distal end 17 of the outer tube 16 and a retracted condition. The atraumatic tip 11 may include a pair of orthogonally disposed slits 13C that divide the tip into four flaps 13b. As the sleeve 13a is retracted proximally, the flaps 13b may separate from one another, thereby exposing the distal end 17 of the outer tube. In a particular embodiment, the outer tube 16 may be made of one or more echogenic materials, so that the outer tube may be more easily visualized inside a patient using three-dimensional echocardiography.

Figure 3A:
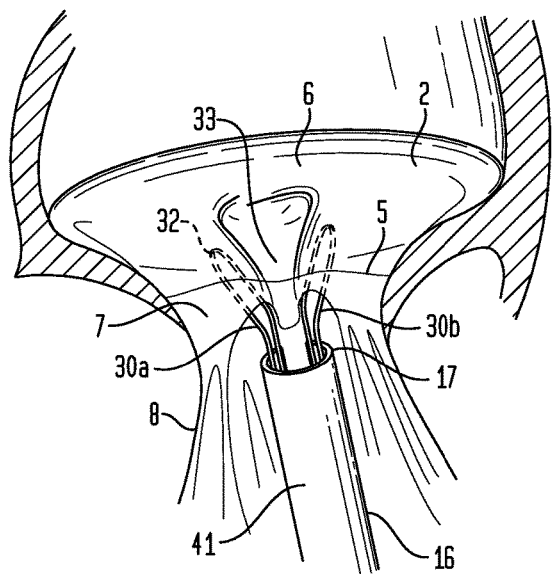
Figure 3B:
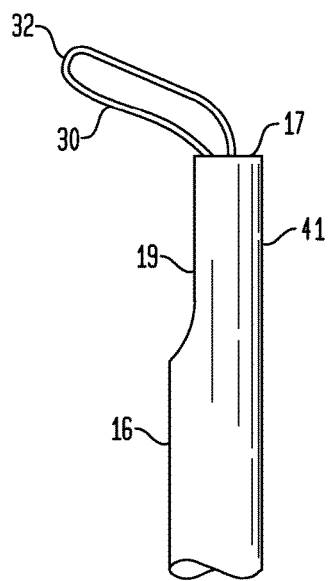
FIG. 3B is a side view of the distal portion of the device of FIG. 2A, shown with the support loops deployed as in FIG. 3A.
Figure 5A:
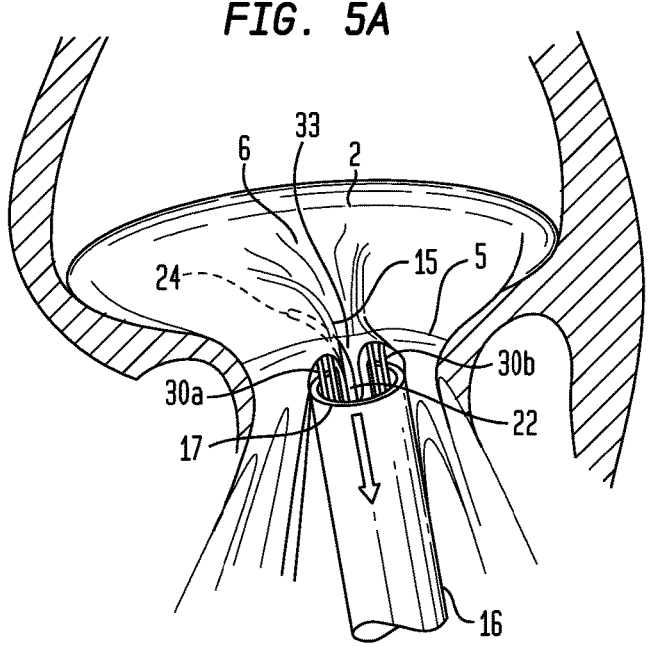
Figure 5B:
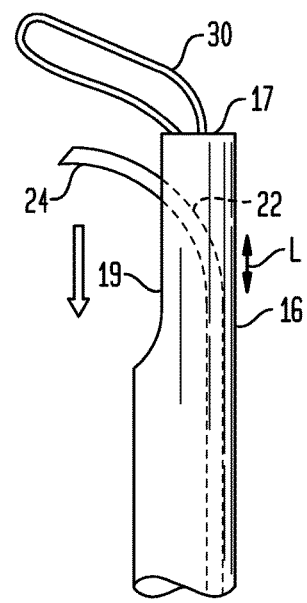
FIG. 5B is a side view of the distal portion of the device of FIG. 2A, shown with the support loops deployed and the hook in a partially-retracted position as in FIG. 5A.
Figure 5F:
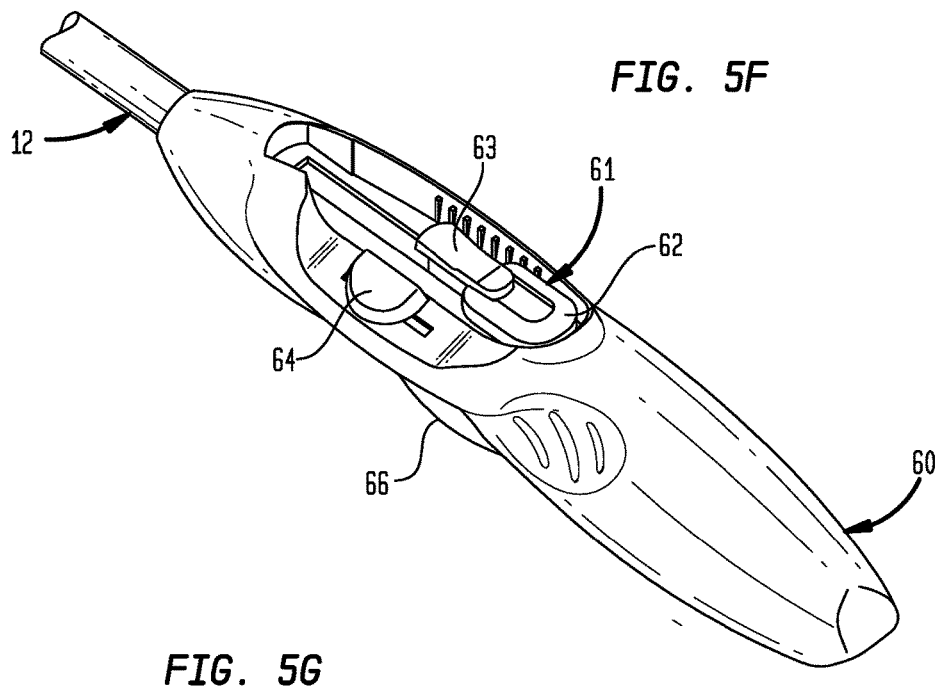
FIG. 5F is a perspective view of the handle of FIG. 2C, shown with the buttons positioned to correspond to the positions of the components of the device shown in FIG. 5A.

The catheter assembly 12 further includes tissue support members in the form of substantially closed loops 30a and 30b (collectively, loops 30) that are longitudinally slidable within respective containment tubes 35a and 35b (collectively, containment tubes 35) disposed within the outer tube 16, all of which can be seen in FIGS. 5C and 5D. The loops 30 are slidable between an initial position retracted within the containment tubes 35 (FIG. 2A) and a tissue-supporting position extending outwardly from the containment tubes (FIGS. 3A and 3B). The loops 30 may have a substantially linear configuration when fully retracted within the containment tubes 35 and may bend laterally away from the closed side 41 of the outer tube when deployed from the containment tubes. In the deployed position, the loops 30 may be spaced from one another so as to define a gap 33 between their closed distal ends 32. The loops 30 may be formed from a memory metal or a strong, resilient metal or polymer that will cause the loops to automatically bend laterally away from the closed side 41 of the outer tube 16 when deployed.

Figure 4A:
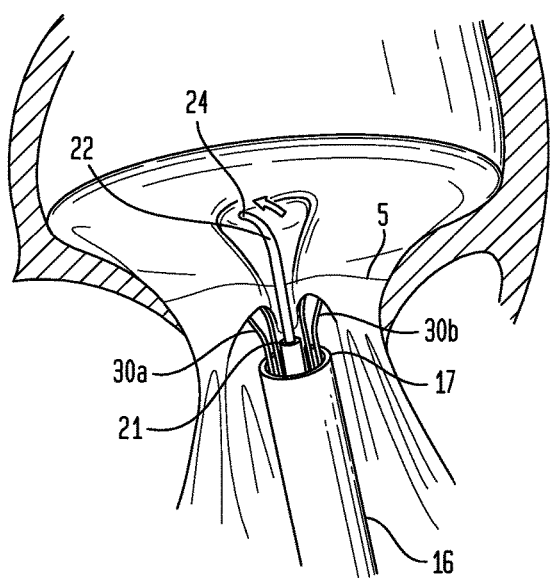
Figure 4B:
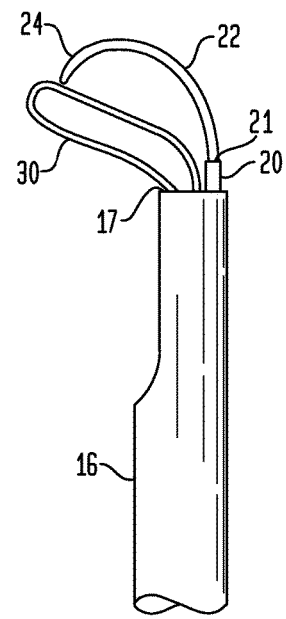
FIG. 4B is a side view of the distal portion of the device of FIG. 2A, shown with the support loops and hook deployed as in FIG. 4A.

A capture tool in the form of a grasping wire 22 may be slideably arranged in a containment tube 20 disposed within the outer tube 16. The grasping wire 22 may be longitudinally slidable within the containment tube 20 between a retracted position substantially within the lumen of the containment tube, and a deployed position in which a distal portion of the grasping wire protrudes from the containment tube. The containment tube 20 may also be longitudinally slideable between a retracted position within the outer tube and a deployed position in which a distal tip 21 of the containment tube protrudes distally beyond the distal end 17 of the outer tube (FIGS. 4A and 4B). The grasping wire 22 may have a linear configuration when fully retracted within the containment tube 20, and the distal portion thereof may assume the shape of a hook 24 when deployed from the containment tube. In that regard, the grasping wire 22 may be formed from a memory metal or a strong, resilient metal or polymer that will cause the hook 24 to form automatically when deployed.

Figure 6A:
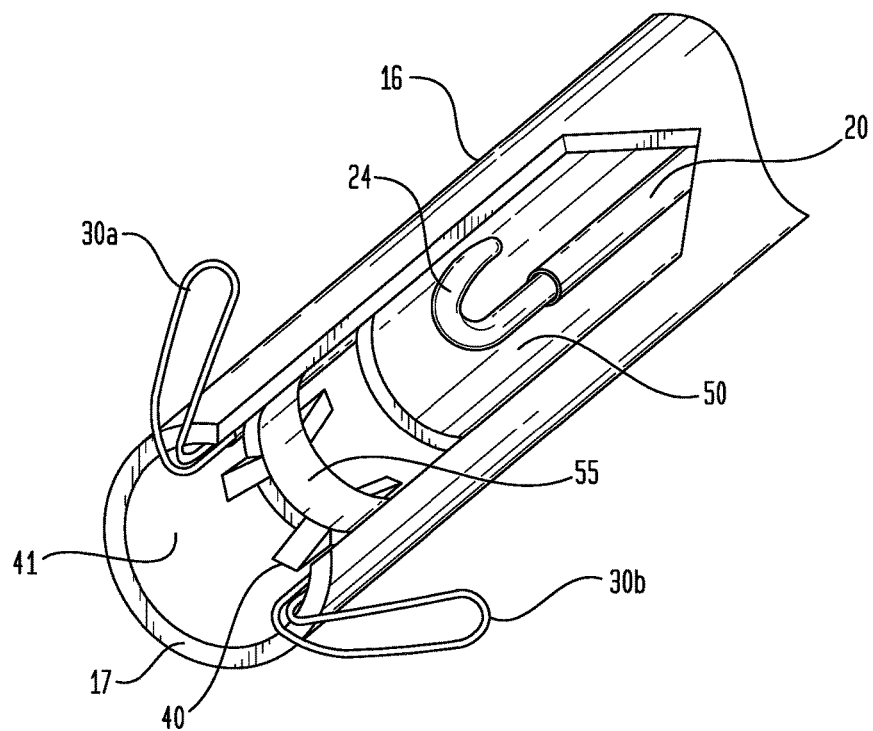
FIG. 6A is a perspective end view of the distal portion of the device of FIG. 2A, shown with the support loops deployed, the hook in a partially-retracted position, and the retaining arm in the retracted position.

A retaining arm 50 may also be disposed within the outer tube 16 and may be longitudinally slidable therein between an initial or distal position, shown in FIG. 5D, and a retracted or proximal position, shown in FIG. 6A. In the initial position, the retaining arm 50 engages a clip 55 disposed adjacent the retaining arm, holding it in place against the closed side of 41 of the outer tube 16. The retraction of the retaining arm 50 releases the clip 55 for application to tissue.

The clip 55 may be supported in the longitudinal direction L during the sliding movement of the retaining arm 50 by a series of ribs 40 provided on the closed side 41 of the outer tube 16 so as to lie between the closed side and the retaining arm when the retaining arm is in the initial position. The ribs 40 may be separated in the longitudinal direction L by a gap 42 sized to receive the clip 55 when the retaining arm is in the initial position.

The clip 55 may be made of a memory metal and may be biased to curl into a substantially round configuration (FIG. 7) when the retaining arm 50 is retracted proximally and the no longer overlies the clip. Each end of the clip 55 may include a prong 56 adapted to become embedded in the leaflet tissue when the clip is deployed.

Figure 2C:
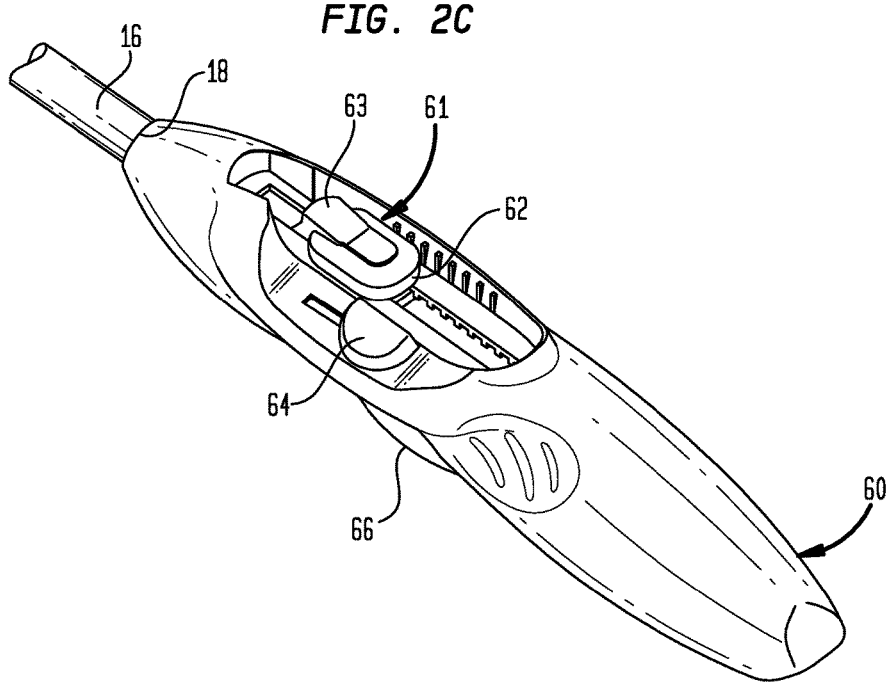
FIGS. 2C and 2D are a perspective view and a longitudinal cross-sectional view of one embodiment of a handle suitable for controlling the device of FIG. 2A, shown with the buttons positioned to correspond to the positions of the components of the device shown in FIG. 2A.
Figure 2D:
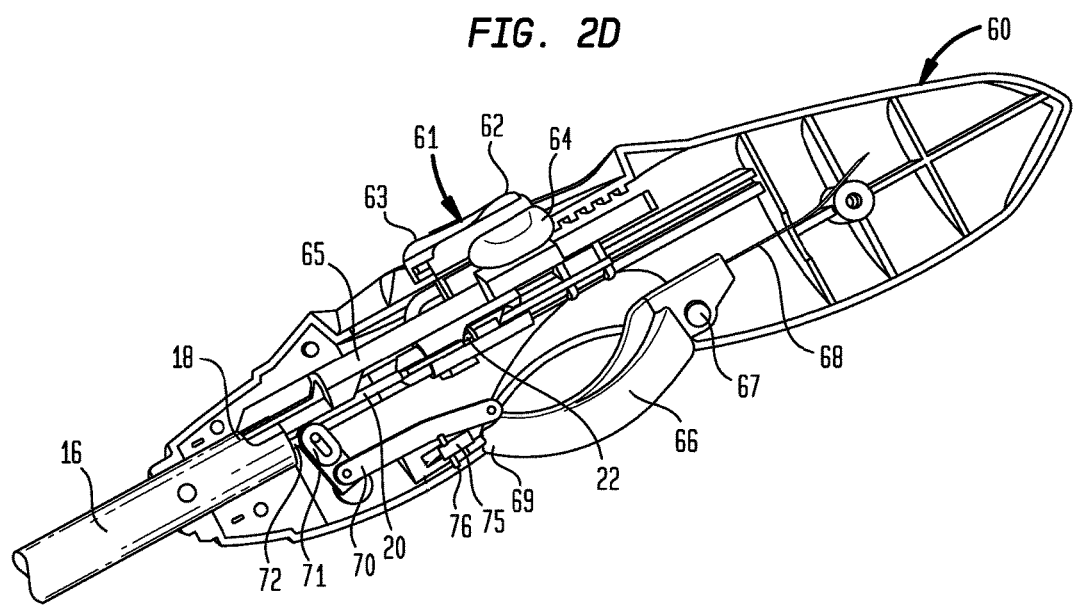

Referring now to FIGS. 2C and 2D, a handle 60 may be provided at the proximal end 18 of the outer tube 16 for operating the device 10. The handle 60 may include a first button 61, a second button 64, and a third button 66 for controlling the operation of the containment tube 20 and the grasping wire 22, the loops 30, and the retaining arm 50, respectively.

The first button 61 may have a first portion 62 and a second portion 63 that are moveable longitudinally relative to the handle 60 and relative to one another. The first portion 62 may be operatively connected to the containment tube 20, such that sliding movement of the first portion in a proximal or distal direction results in a corresponding sliding movement of the containment tube. The second portion 63 may be operatively connected to the grasping wire 22, such that sliding movement of the second portion in a proximal or distal direction results in a corresponding sliding movement of the grasping wire. The containment tube 20 and the grasping wire 22 may be moved together by the simultaneous movement of the first and second portions of the button 61. Alternatively, the containment tube 20 and the grasping wire 22 may be moved independently of one another by moving one of the portions of the button 61 while the other portion remains stationary. For example, sliding the second portion 63 distally while the first portion 62 remains stationary advances the grasping wire 22 out from the containment tube 20, resulting in deployment of the hook 24.

The second button 64 may be moveable longitudinally relative to the handle 60 for controlling the movement of the loops 30 relative to the outer tube 16. The second button 64 may be operatively connected to one end of a linkage 65, the other end of which may be operatively connected to the loops 30, such that sliding movement of the second button in a proximal or distal direction results in a corresponding sliding movement of the loops.

Figure 5G:
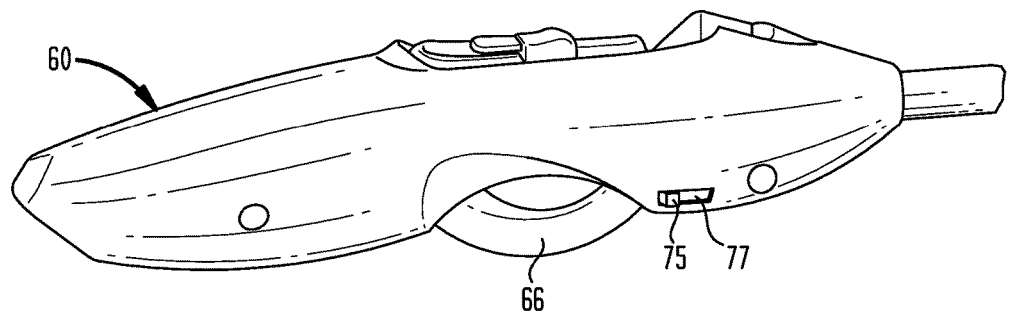
FIGS. 5G and 5H are a perspective view and a longitudinal cross-sectional view of the handle of FIG. 2C, shown with the buttons positioned to correspond to the positions of the components of the device shown in FIG. 5A.
Figure 5H:
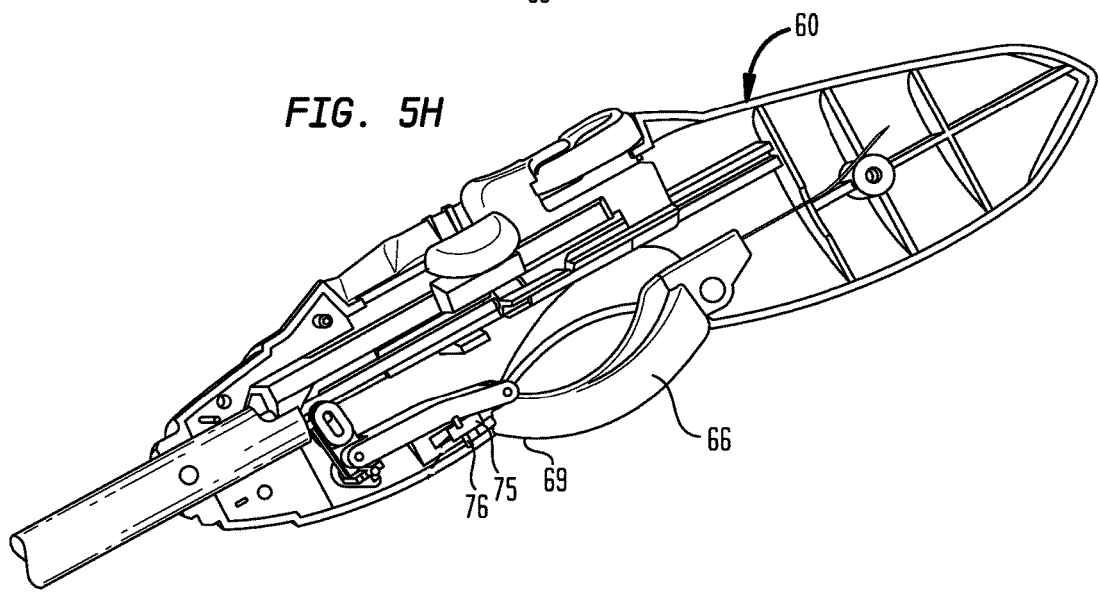
Figure 6B:
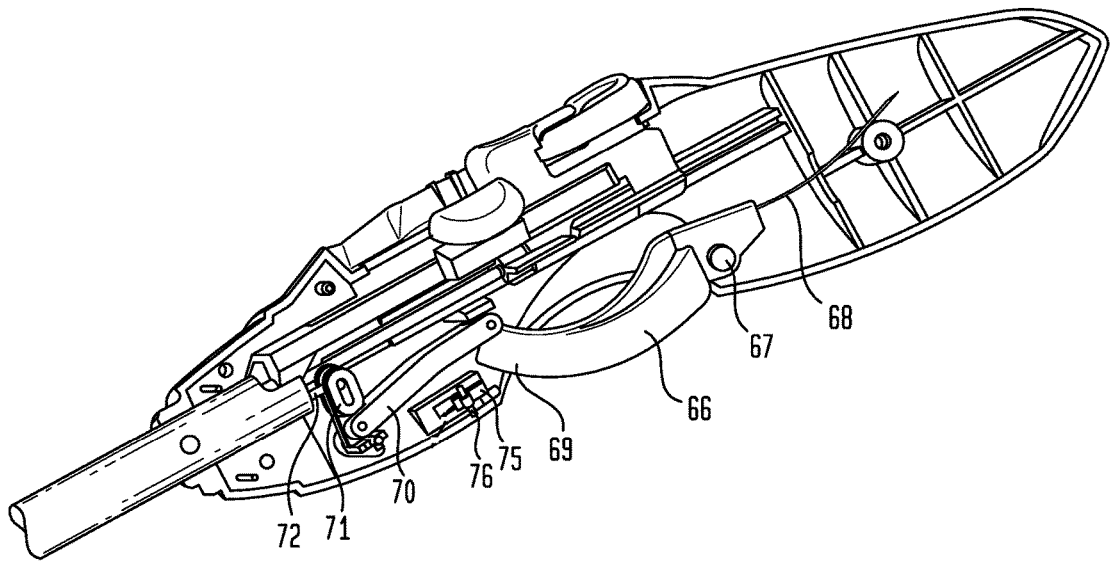
FIG. 6B is a longitudinal cross-sectional view of the handle of FIG. 2C, shown with the buttons positioned to correspond to the positions of the components of the device shown in FIG. 6A.

The third button 66 may have a trigger shape and may be connected at one end to the handle 60 by a pivot pin 67 that allows for movement of the button in a lateral direction relative to the longitudinal axis of the handle for controlling the movement of the retaining arm 50 relative to the outer tube 16. A spring 68 may bias the third button 66 to return to its initial position (FIG. 2D) after the button has been actuated (FIG. 6B). The opposite end 69 of the third button 66 may be pivotally coupled to a linkage assembly including a first linkage 70, a second linkage 71, and a third linkage 72, all of which are pivotally connected to one another in series. The third linkage 72 may be connected to the proximal end of the retaining arm 50, such that actuation of the third button 66 may cause the third linkage 72 to slide proximally to retract the retaining arm and thereby deploy the clip 55. A safety catch 75 may be connected to the handle 60 by a pivot pin 76, such that the safety catch may rotate between a locked position (FIGS. 5G and 5H) that prevents actuation of the third button 66 and an unlocked position (FIG. 6B) that frees the third button for actuation.

To use the device 10 for gathering of heart valve leaflet tissue, a user may first actuate the third button 66 of the handle 60 to retract the retaining arm 50 proximally of the gap 42 between the ribs 40. A clip 55 may then be loaded into the gap 42, and the third button 66 may be released. The spring 68 will bias the third button 66 back to its initial position, whereupon the retaining arm 50 will slide distally until it covers the clip 55 and holds it in place.

Next, referring to FIG. 2A, the distal portion 14 of the catheter assembly 12 may be inserted into the left ventricle of a patient, for example, through the apex of the heart, so that the distal portion extends between the posterior leaflet 2 and the anterior leaflet 3 of the mitral valve 1. As shown in FIG. 2A, the distal end 17 of the outer tube 16 may be disposed proximally of the coaption line 5 of the mitral valve 1, with the open side 19 of the outer tube facing the posterior leaflet 2. The distal end 17 of the outer tube 16 may be guided to a desired position relative to the coaption line 5 using the assistance of three-dimensional echocardiography to visualize the outer tube or other components of the catheter assembly 12. Once the distal end 17 of the device is in a desired position, the sleeve 13a of the atraumatic tip 11 may be slid proximally until the flaps 13b are proximal of the open side 19 of the outer tube 16, exposing the inner components of the device 10 for deployment.

Figure 4C:
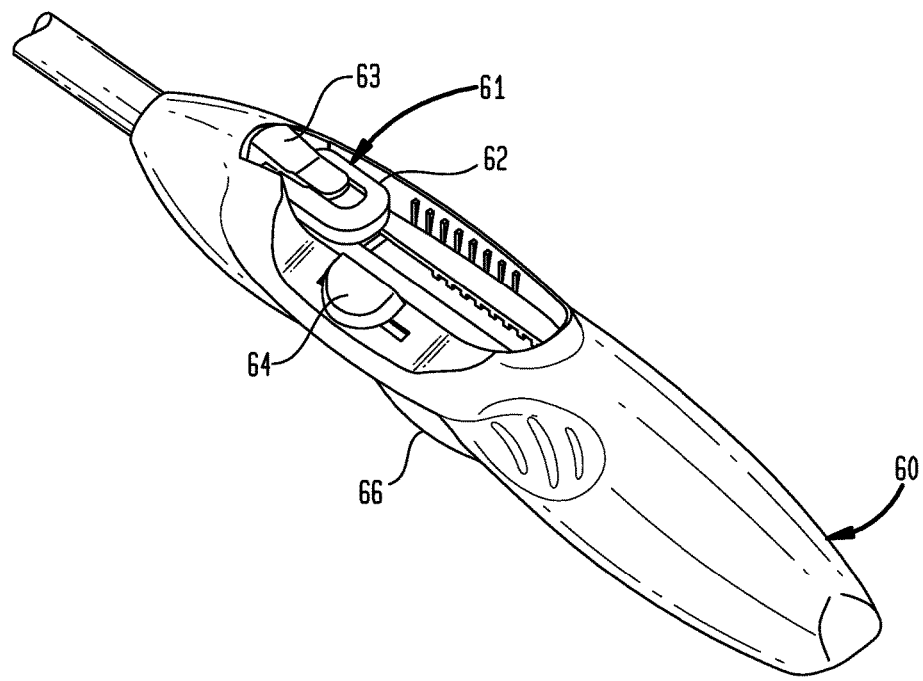
FIGS. 4C and 4D are a perspective view and a longitudinal cross-sectional view of the handle of FIG. 2C, shown with the buttons positioned to correspond to the positions of the components of the device shown in FIG. 4A.

Then, referring to FIGS. 3A and 3B, the loops 30 may be deployed by sliding the second button 64 distally from an initial position (shown in FIG. 2C) to a deployed position (shown in FIG. 4C). The distal movement of the second button 64 moves the loops 30 distally relative to the outer tube 16 and the containment tubes 35. As the loops 30 move distally, the memory of the material forming the loops will cause the ends 32 of the loops to bend laterally away from the closed side 41 of the outer tube 16 and away from one another to expand the internal gap 33 between the loops. Preferably, the outer tube 16 is positioned against or close to the chordae tendineae 8 so that, as the loops 30 are deployed, the ends 32 of the loops will extend along the bottom surface of the posterior leaflet 2 under both the upper portion 6 and the lower portion 7 and between adjacent ones of the chordae tendineae 8. As the loops 30 are positioned, the free edge of the posterior leaflet 2 may slide over the loops towards the containment tubes 35, such that tissue of the posterior leaflet overlies the distal end 17 of the outer tube 16.

Referring next to FIGS. 4A and 4B, the containment tube 20 may be deployed by sliding the first and second portions 62 and 63 of the first button 61 together distally to move the containment tube from an initial position (not shown) to a deployed position (shown in FIG. 4A). The distal movement of the first button 61 moves the tip 21 of the containment tube 20 beyond the distal end 17 of the outer tube 16, such that the tip 21 moves closer to the coaption line 5.

Figure 4D:
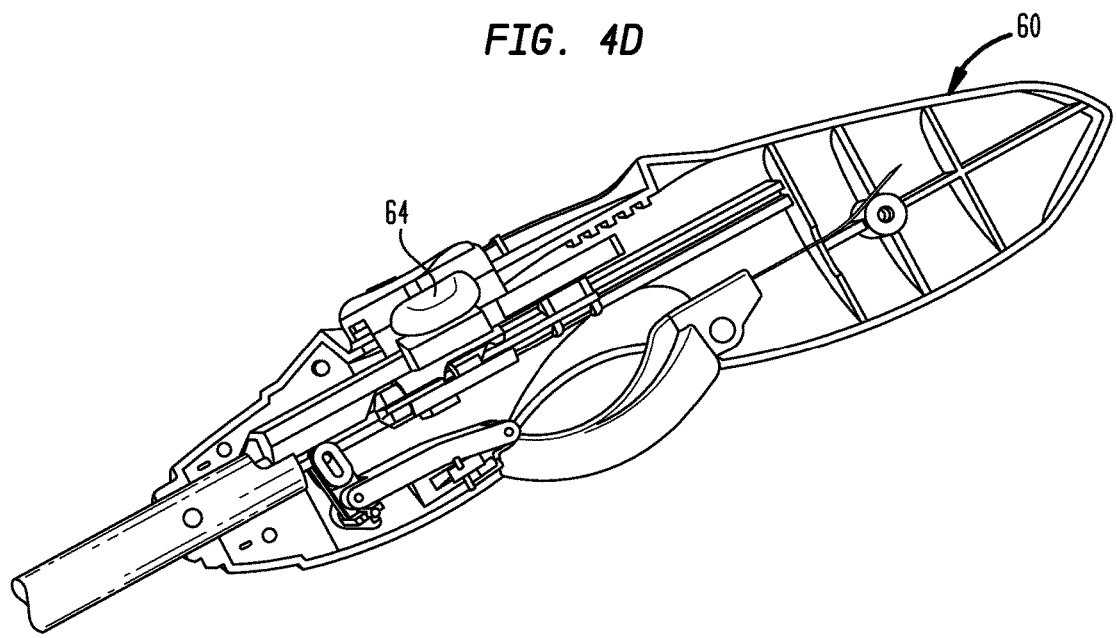

The hook 24 may then be deployed to an extended position by sliding the second portion 63 of the first button 61 distally relative to the first portion 62 from an initial position (shown in FIG. 2C) to a deployed position (shown in FIGS. 4C and 4D). The distal movement of the second portion 63 relative to the first portion 62 moves the distal portion of the grasping wire 22 out of the containment tube 20. No longer being constrained by the containment tube 20, the distal portion of the grasping wire 22 may assume the curved shape of the hook 24.

The hook 24 of the grasping wire 22 may be used to grasp tissue of the posterior leaflet 2 and pull it into the distal end of the outer tube 16. Referring to FIGS. 5A-5F, the hook 24 may be partially retracted against the tissue of the posterior leaflet 2 by sliding the first and second portions 62 and 63 of the first button 61 together proximally. The proximal movement of the first button 61 partially retracts the containment tube 20, and with it the grasping wire 22, such that the hook 24 engages against the upper surface 6 of the posterior leaflet 2 and pulls tissue of the leaflet through the gap 33 between the loops 30a and 30b. As the hook 24 continues to retract proximally between the loops 30a and 30b, captured tissue 15 of the posterior leaflet 2 will be forced between the loops and into the distal end of the outer tube 16.

A V-shaped pleat 80 will thus be formed in the captured tissue 15. The pleat 80 will have a V-shape in longitudinal cross-section, as shown in FIG. 5E, with the lowered center portion of the V underlying the hook 24, and the two upper portions of the V overlying the loops 30a and 30b. The pleat 80 will also have a V-shape in transverse cross-section as evident in FIG. 5C, with the lowered center portion of the V extending around the end 25 of the hook 24, and the two upper portions of the V extending from the end of the hook toward the closed side 41 of the outer tube 16. By forming a V-shaped pleat 80, most or all of the portion of the posterior leaflet 2 that is billowed, loose, or floppy may be gathered and tightened.

Figure 7:
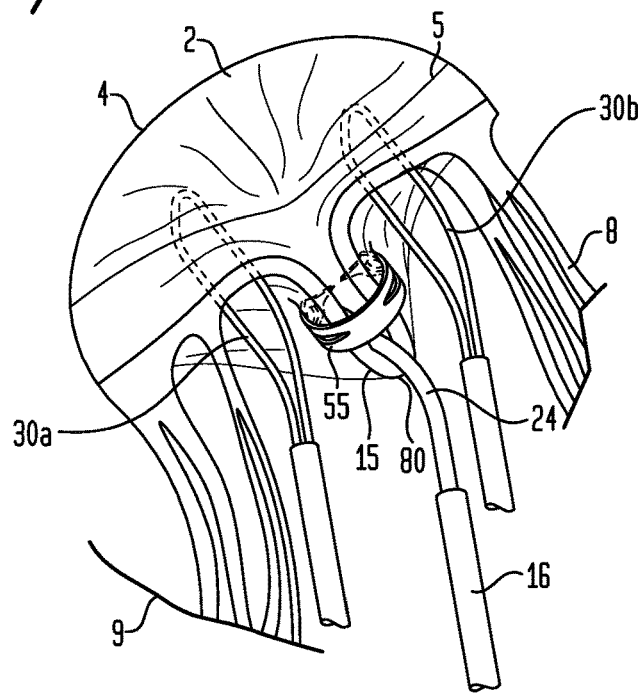
FIG. 7 is a diagrammatic view of the clip and the posterior mitral valve leaflet of FIG. 5C, shown with the clip in a deployed position.

With some of the tissue of the posterior leaflet 2 captured within the distal end of the outer tube 16, the retaining arm 50 may be retracted by releasing the catch 75 and actuating the third button 66 by depressing it toward the handle 60. The retaining arm 50 may be retracted until it is proximal of the gap 42 between the ribs 40, as shown in FIG. 6A. At this juncture, the retaining arm 50 will no longer overlie the clip 55, such that the two prongs 56 of the clip will be free to spring away from the closed surface 41 of the outer tube 16 and become embedded in the captured tissue 15 of the posterior leaflet 2, thereby securing the tissue in the pleated form. As can be seen in FIG. 7, the clip 55 may pierce tissue of the posterior leaflet 2 from the bottom surface of the leaflet, thereby retaining the captured tissue 15 in the V-shaped pleat 80. The clip 55 may be engaged in the lower portion 7 of the posterior leaflet 2 close to the coaption line 5. The two prongs 56 may overlap one another, and the clip 55 may extend along an arc that is greater than 360 degrees.

A suture (not shown) may extend between the clip 55 and the catheter assembly 12 so that the clip may be retrieved using the device 10, for example, if the clip has been installed at a sub-optimal location on the posterior leaflet 2 or does not become adequately embedded in the tissue. A user may desire to disengage the clip from the tissue and deploy another one.

After the clip 55 has been adequately secured in the tissue of the posterior leaflet 2, the device 10 may be withdrawn from the patient. To withdraw the device 10, the hook 24 may first be withdrawn from engagement with the posterior leaflet 2 by retracting the second portion 63 of the first button 61 relative to the first portion 62 thereof. This action causes the hook 24 to straighten as the grasping wire 22 retracts into the containment tube 20.

Next, the loops 30 may be withdrawn from engagement with the posterior leaflet 2 by moving the second button 64 proximally, thereby retracting the loops into the containment tubes 35. As the loops 30 retract, the ends 32 of the loops will move out from under the posterior leaflet 2.

Figure 8:
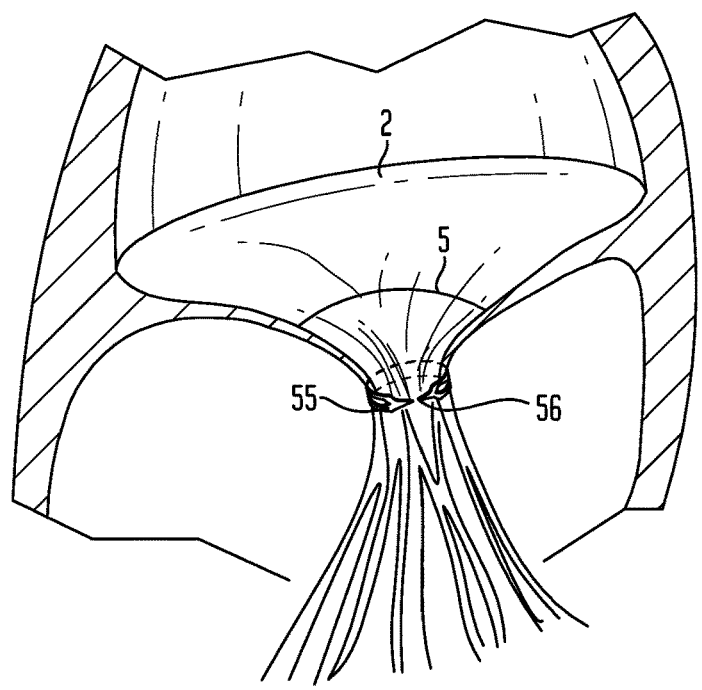
FIG. 8 is a view similar to FIGS. 2A, 3A, 4A, and 5A, showing the clip in a deployed position.

Once the hook 24 and the loops 30 have disengaged from the posterior leaflet 2, the posterior leaflet may assume its natural orientation, such as that shown in FIG. 8. The clip may have an installed orientation that is different than that shown in FIG. 7, such that the prongs 56 may point toward the anterior leaflet 3, while the center of the clip faces away from the anterior leaflet.

Finally, the catheter assembly 12 may be withdrawn from the patient through the apex of the heart. The procedure described above may be repeated to apply one or more additional clips 55 onto the same posterior leaflet 2.

In the foregoing, particular structures have been described that are adapted to gather, secure, and repair heart valve leaflet tissue. The invention also contemplates the use of any alternative structures for such purposes, including structures having different lengths, shapes, and configurations. For example, although the catheter assembly is described as being controllable by the movement of a particular configuration of buttons 61, 64, and 66 of the handle 60, any mechanisms that are adapted to control the movement and deployment of the containment tube 20, grasping wire 22, loops 30, and clip 55 may be used.

Furthermore, although the capture tool is shown as a single grasping wire 22 having a single hook 24 that cooperates with support members shown in the form of two loops 30 to capture leaflet tissue and form same into a V-shaped pleat 80, the capture tool and support members may have any shape or configuration that may be adapted to cooperate to grasp a target portion of valve leaflet tissue and to capture such tissue, forming any number of pleats therein, such that a clip may be applied to the captured tissue. For example, a support member having a single loop may cooperate with two hooks that are laterally spaced apart from one another to form leaflet tissue into a pleat, or a single hook may cooperate with a single loop, the sides of which are spaced apart sufficiently to form leaflet tissue into a pleat therebetween. The invention contemplates support members having any number of hooks cooperating with any number of loops to form any number of pleats in the captured tissue. It will be appreciated that the more pleats that are formed, the more the tissue of the valve leaflet can be tightened.

Moreover, although the capture tool has been described as a grasping wire 22, it may take other forms, including for example, a pincer-like structure such as a clamp, or any other structure that can guide leaflet tissue into a fold or pleat onto which a clip can be attached. Also, the support members may have other configurations, such as the solid tines of a fork, an arm having a curved surface such that outer edges of the arm can serve as loops, a lattice structure, or any other structure capable of supporting the leaflet tissue against the force exerted by retraction of the hook.

Although the catheter assembly 12 has been described as including ribs 40 on the closed side 41 of the outer tube 16 for holding the clip 55 in place, that need not be the case. Rather, a recess may be formed in the closed side 41 of the outer tube 16 for receiving the clip. Further, although the retaining arm 50 has been described as engaging the clip when the retaining arm is in the distal position and releasing the clip when the retaining arm is in the proximal position, the invention contemplates an alternative retaining arm that retains the clip when the retaining arm is in a proximal position and releases the clip when the retaining arm is moved to a distal position.

Although the loops 30 have been described as being made from a memory metal so that the closed ends 32 of the loops automatically bend laterally away from the closed side 41 of the outer tube 16 when the loops are extended distally from the outer tube, other mechanisms may be used for controlling such lateral movement of the ends of the loops. For example, support members such as the loops 30 or support members having other structures may be made of a non-memory material, and cam surfaces within the outer tube 16 may guide the support members as they are deployed and retracted. Alternatively, a mechanism controlled by a dedicated button of the handle may be used to actuate lateral movement of the closed ends 32 of the loops 30 relative to the outer tube 16.

Although the device 10 has been described in connection with the application of a single clip 55 onto a posterior leaflet 2, the invention contemplates devices that are adapted to apply a plurality of clips to the leaflet tissue during a single insertion of the device into a patient. For example, the gap 42 between the ribs 40 may be sufficiently large to accommodate a plurality of clips 55 in side-by-side relationship in the longitudinal direction of the outer tube 16, or a series of ribs 40 may be formed along the length of the outer tube 16, with a gap 42 sized to receive an individual clip being defined between each adjacent pair of ribs. In such embodiments, while leaflet tissue is captured between the hook 24 and the loops 30, the retaining arm 50 may be retracted to a first position to apply a first clip 55 to the tissue at a first target location and may then be further retracted to a second position to apply a second clip 55 to the tissue at a second target location spaced from the first location.

Although the various delivery devices have been described herein in connection with tightening the posterior leaflet of a mitral valve, all of the delivery devices may be used on other heart valve leaflets, such as the anterior leaflet of the mitral valve, or on any other tissue of the body for which a reduction in the length of the tissue would be beneficial.

Although the invention herein has been described with reference to particular embodiments in which the catheter assembly is inserted into the patient through the apex of the heart (i.e., transapical insertion), it is to be understood that the invention contemplates embodiments in which the catheter assembly extends through another portion of the heart, through a portion of the vasculature of the patient to reach the heart, for example, through a transfemoral or subclavian artery, or through the aorta. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

INDUSTRIAL APPLICABILITY

The present invention enjoys wide industrial applicability including, but not limited to, methods and devices for gathering tissue in a patient.

The invention claimed is:

1. A device for gathering tissue of a heart valve leaflet, the device comprising:
    an elongated tube extending in a longitudinal direction and having a tube wall defining a lumen, a distal end of the tube wall having a slot extending in the longitudinal direction, the slot having an open end at the distal end of the tube wall and a closed end;
    a tissue support member moveable relative to the tube between a retracted position and an extended position, the tissue support member having at least two spaced apart support elements disposed on opposite sides of the slot, each support element including a closed loop having a distal end, the distal ends of the closed loops being spaced from one another by a gap; and
    a capture tool moveable relative to the tube and between the support elements between a retracted position and an extended position, a distal end of the capture tool being movable in the longitudinal direction through the slot from the extended position disposed above a distal end of the tissue support member to the retracted position disposed below a distal end of the tissue support member,
    the capture tool and the tissue support member being operable to capture tissue of the heart valve leaflet therebetween, such that the captured tissue has a gathered configuration.

2. The device as claimed in claim 1, wherein the support elements are made from a memory metal.

3. The device as claimed in claim 1, wherein the gathered configuration is in the shape of a V.

4. The device as claimed in claim 1, wherein the elongated tube extends in a longitudinal direction, and distal ends of the support elements are adapted to move laterally away from the capture tool in a direction transverse to the longitudinal direction when the support elements move from the retracted position to the extended position.

5. The device as claimed in claim 1, further comprising an operating handle having an actuating member adapted to control movement of the tissue support member between the retracted and extended positions.

6. The device as claimed in claim 1, wherein the distal end of the capture tool has a hook shape in the extended position.

7. The device as claimed in claim 1, wherein the capture tool includes a grasping wire slidably disposed in a containment tube, and a distal portion of the grasping wire is adapted to change from a linear shape to a hook shape when the distal portion of the grasping wire is extended out from the containment tube.

8. The device as claimed in claim 7, wherein the grasping wire is made from a memory metal.

9. The device as claimed in claim 7, further comprising an operating handle having an actuating member adapted to control movement of the grasping wire between retracted and extended positions and movement of the containment tube between retracted and extended positions.

10. The device as claimed in claim 9, wherein operation of the actuating member controls simultaneous movement of the grasping wire and the containment tube.

11. The device as claimed in claim 9, wherein the actuating member has first and second portions that are moveable relative to one another, the first portion being adapted to control movement of the grasping wire and the second portion being adapted to control movement of the containment tube.

12. The device as claimed in claim 11, wherein the first portion is adapted to control movement of the grasping wire independently of movement of the containment tube.

13. The device as claimed in claim 1, further comprising a releasable clip adapted to be applied to the tissue for holding the tissue in the gathered configuration.

14. The device as claimed in claim 13, further comprising a retaining arm moveable between a first position for retaining the clip and a second position for releasing the clip for application to the tissue.

15. The device as claimed in claim 14, wherein the clip is biased from an open condition to a clamping condition, the retaining arm in the first position holding the clip in the open configuration, and the retaining arm in the second position releasing the clip for application to the tissue.

16. The device as claimed in claim 14, further comprising an operating handle having an actuating member adapted to control movement of the retaining arm between the first position and the second position.

* * * * *